United States Patent
Gouch et al.

(10) Patent No.: US 10,241,310 B2
(45) Date of Patent: Mar. 26, 2019

(54) METHOD OF FORMING AN IMAGING CALIBRATION DEVICE

(71) Applicant: FFEI Limited, Hemel Hempstead (GB)

(72) Inventors: Martin Philip Gouch, Hemel Hempstead (GB); Craig Revie, Hemel Hempstead (GB); Peter Walsh, Hemel Hempstead (GB); Jacqueline Margaret Deane, Hemel Hempstead (GB)

(73) Assignee: FFEI Limited, Hertfordshire (GB)

( * ) Notice: Subject to any disclaimer, the term of this patent is extended or adjusted under 35 U.S.C. 154(b) by 409 days.

(21) Appl. No.: 14/407,508

(22) PCT Filed: Jun. 3, 2013

(86) PCT No.: PCT/GB2013/051471
§ 371 (c)(1),
(2) Date: Dec. 12, 2014

(87) PCT Pub. No.: WO2013/186530
PCT Pub. Date: Dec. 19, 2013

(65) Prior Publication Data
US 2015/0192765 A1      Jul. 9, 2015

(30) Foreign Application Priority Data

Jun. 13, 2012  (GB) .................................. 1210403.0
Sep. 7, 2012   (GB) .................................. 1216022.2

(51) Int. Cl.
*G02B 21/00* (2006.01)
*G01N 21/27* (2006.01)
(Continued)

(52) U.S. Cl.
CPC .......... *G02B 21/0096* (2013.01); *G01N 1/30* (2013.01); *G01N 1/312* (2013.01); *G01N 21/278* (2013.01); *G06T 7/80* (2017.01)

(58) Field of Classification Search
USPC .......................................................... 348/79
See application file for complete search history.

(56) References Cited

U.S. PATENT DOCUMENTS

| 5,428,690 A    | 6/1995 | Bacus et al. |
| 6,615,141 B1 * | 9/2003 | Sabry ................. G06K 9/00127 382/133 |

(Continued)

FOREIGN PATENT DOCUMENTS

| DE | 103 52 123 A1 | 8/2004 |
| EP | 0 557 871 A2  | 9/1993 |
| WO | 2006/007766 A1 | 1/2006 |

OTHER PUBLICATIONS

International Search Report for PCT/GB2013/051471 dated Aug. 21, 2013.

*Primary Examiner* — Chikaodili E Anyikire
(74) *Attorney, Agent, or Firm* — Sughrue Mion, PLLC (57) ABSTRACT

A method of forming an imaging calibration device for a biological material imaging system, the method comprises: providing one or more discrete regions upon or within a retaining member, each region for the receipt of a selected predetermined biological stain material; selecting one or more predetermined biological stain materials, wherein each of the selected predetermined biological stain materials has a predetermined optical response, and providing one or more of the selected predetermined biological stain materials to the said one or more discrete regions such that the said material is localised in the said region.

27 Claims, 4 Drawing Sheets

(51) Int. Cl.
*G01N 1/30* (2006.01)
*G01N 1/31* (2006.01)
*G06T 7/80* (2017.01)

(56) References Cited

U.S. PATENT DOCUMENTS

| | | | | |
|---|---|---|---|---|
| 2003/0124733 | A1* | 7/2003 | Bushway | G01N 33/54393 |
| | | | | 436/174 |
| 2003/0231791 | A1* | 12/2003 | Torre-Bueno | G01N 21/6428 |
| | | | | 382/133 |
| 2004/0085443 | A1* | 5/2004 | Kallioniemi | G01N 1/36 |
| | | | | 348/135 |
| 2007/0037138 | A1* | 2/2007 | Winther | G01N 15/1468 |
| | | | | 435/5 |
| 2007/0292941 | A1* | 12/2007 | Handique | B01L 3/5027 |
| | | | | 435/288.7 |
| 2009/0189972 | A1* | 7/2009 | Harris | A61B 5/0059 |
| | | | | 348/14.08 |
| 2011/0318226 | A1* | 12/2011 | Ge | G01N 21/278 |
| | | | | 422/63 |
| 2014/0038206 | A1* | 2/2014 | Holmes | G01N 21/17 |
| | | | | 435/7.21 |

\* cited by examiner

| Stain type |
|---|
| H&E (hematoxylin and eosin) |
| Silver |
| Prussian Blue |
| Sudan |
| PAS (Periodic acid-Schiff) |
| Congo Red |
| Gramms (Crystal violet and Safranin) |
| Ziehl–Neelsen |
| Auramine-Rhodamine |
| Warthin–Starry |
| Neutral Red |
| Janus Green B |

METHOD OF FORMING AN IMAGING CALIBRATION DEVICE

CROSS REFERENCE TO RELATED APPLICATIONS

This application is a National Stage of International Application No. PCT/GB2013/051471 filed Jun. 3, 2013, claiming priority based on United Kingdom Patent Application Nos. 1210403.0, filed Jun. 13, 2012 and 1216022.2, filed Sep. 7, 2012, the contents of all of which are incorporated herein by reference in their entirety.

The invention relates to a method of forming an imaging calibration device and, in particular, an imaging calibration device for a biological material imaging system.

In histopathology, there are well known methods of obtaining the anatomy of biological materials such as tissue or cells at microscopic scales. Typical methods for analysing cells involve the preparation of cells by sectioning and staining the cells and then examining the stained cells under a light microscope by a histopathologist. Staining using stains or dyes is an auxiliary technique commonly used in microscopy to enhance contrast in the microscopic image. Different cell types may be combined with different stains of different colours so that the colour of the stained cell may indicate what type or group a cell is. This enables diagnosis of abnormalities or diseases.

The colour produced by each tissue preparation depends on the type of tissue and the strength of the stain used. For example a thick tissue stained with a stain of higher concentration will produce a stronger colouration, whilst a thin tissue a stained with a stain of lower concentration will produce a weaker colouration. This difference in staining strengths is important and can influence the diagnostic result a histopathologist decides upon. Thus it is common in this area for the preparation of the stained cells to be standardised, either within a laboratory or between laboratories.

In modern laboratories it has become common practice to view a sample of cells with a digital camera attached to a microscope or to use a very high resolution scanner to digitally reproduce the appearance of the cells over a larger area. This enables the images to be shared between histopathologists without the need for them to be looking down the same microscope at the same sample. A problem with this practice, however, is that the colour appearance of the cells has an additional variation added by the colour response of the microscope, digital camera or scanner and the colour monitor or printer being used to view the image, as each of these devices has its own colour response.

The variation in colour appearance due to different measuring and reproduction equipment is a problem commonly encountered in the graphic arts. This problem is normally addressed by using a standardised calibration process as defined by the International Color Consortium, ICC. This is a standardised way of translating digital values read by a device or equipment into colour measurements defined by the Commission Internationale de l'Eclairage, CIE. The ICC defines a file format which can be used to link the device colour values to an interchange space in device independent CIE colour coordinates. Thus a colour produced by one measurement device or reproduction device can be mapped onto another device such that to a human they appear to be the same colour. This file format is commonly referred to as an ICC profile.

In the graphic arts an ICC profile is generated by producing matched pairs of values. The reproduction part of the process, i.e. by monitor display or printing, is common in the graphic arts and the same ICC profiles can be used with the reproduction of microscopy images.

Typically an input device such as a graphic arts scanner or a studio camera is calibrated or characterised by using a colour calibration target. The calibration target typically contains a set of colour patches having a wide range of colours. The colour patches are measured with the input device which usually produces three spectral values for each colour patch, commonly called RGB, or red, green, blue triplets. The same colour patches of the chart are then measured with a spectrometer or other suitable instrument which typically produces 32 sets of spectral numbers across the visible spectrum. These spectral values can then be converted to CIE colour coordinates using the equations defined by the CIE, which are typically triplets such as Lab or XYZ. An ICC profile describes the mapping from the RGB values to the CIE colour values.

The colour patches are normally combined into a mosaic of patches referred to as a calibration chart. Typically this is an IT8 chart as defined by "American National Standards Institute", ANSI, but there are other examples of such calibration charts such as the Gretag Macbeth Color Checker Chart. It is normal for the calibration chart to contain the colours typically presented to the image capture system such as a microscope with an attached digital camera.

The IT8 charts are commonly produced in every type of film substrate used, in order to ensure that the spectral content of each patch is the same as the spectral content of the image being scanned. Otherwise, a phenomenon known as metamerism can cause the ICC profile to correctly calibrate the chart but give different colours for the image being scanned. This phenomenon can occur when the same colour on the chart and the stained cell have a different spectral content, which gives the same CIE colour value but different measured RGB values.

Accordingly, there is a need for a technique which addresses the above issue and reduces the probability of metamerism happening.

In accordance with a first aspect of the invention, there is provided a method of forming an imaging calibration device for a biological material imaging system, the method comprising: providing one or more discrete regions upon or within a retaining member, each region for the receipt of a selected predetermined tissue stain material, wherein every part of the discrete region produces a common optical path length through the region, as defined in the direction normal to the surface of the retaining member; selecting one or more predetermined tissue stain materials, wherein each of the selected predetermined tissue stain materials has a predetermined optical response; and providing one or more of the selected predetermined tissue stain materials in a fluid form to the said one or more discrete regions such that the said material is localised in the said region.

In accordance with a second aspect of the invention, there is provided an imaging calibration device for a biological material imaging system, the device comprising: a retaining member; one or more discrete regions located upon or within the retaining member, each region for the receipt of a selected predetermined tissue stain material, wherein every part of each discrete region has a common optical path length through the region, as defined in the direction normal to the surface of the retaining member; and one or more selected predetermined tissue stain materials received in the said one or more discrete regions such that the said material is localised in the said region, wherein each of the selected predetermined tissue stain materials has a predetermined optical response.

In accordance with a third aspect of the invention, there is provided the use of a device to calibrate a biological material imaging system, the device comprising: a retaining member; one or more discrete regions located upon or within the retaining member, each region for the receipt of a predetermined tissue stain material, wherein every part of each discrete region has a common optical path length through the region, as defined in the direction normal to the surface of the retaining member; and one or more predetermined tissue stain materials received in the said one or more discrete regions such that the said material is localised in the said region.

The imaging calibration device is also referred to herewith as a calibration or colour chart, or a colour calibration target. The biological imaging system may be a microscope, for example. The method of forming the imaging device involves constructing a colour chart onto or within a retaining member, for example a microscope slide, where the localised predetermined biological tissue materials form colour patches of the chart. Advantageously, using predetermined tissue stain materials as colour patches to form a calibration chart enables the colours on the chart and the stained cell imaged with the imaging system to have the same spectral content. This prevents metamerism occurring when the formed imaging calibration device is used to calibrate the imaging system.

For general use with microscope imaging devices, the retaining member is preferably a microscope slide as most microscope imaging devices are arranged to image a microscope slide. The retaining member may be formed of a glass material (i.e. a glass slide) or may be formed from paper, plastic or other material, as may any substrate with which the retaining member is engaged in use. In most cases the calibration device provides for transmissive imaging in which light is passed through the discrete regions (and stain material received in the regions), however, reflective alternatives are also envisaged.

The predetermined biological stain materials may take a number of different forms including stains which are tissue stains, fluorescent markers and so on. The form of the predetermined biological stain materials preferably mimics the form of the stains when in contact with biological material. Accordingly, a biological stain material may be obtained by "pre-reacting" a stain with another chemical (replicating the role of the biological material) so as to "develop" the stain in the form of the biological stain material as applied to the retaining member.

This invention finds its particular benefit in transmissive 'bright field' microscopy systems wherein the entire sample or 'discrete region' is fully illuminated by a light source. As this light passes through the sample, in this case a discrete region containing a tissue stain material, certain wavelengths are absorbed or blocked by the stain material (and any other matter in the field of view). The remaining "coloured" light (having a spectrum resulting from the interaction between the incident light, stain material and possibly the "sample" material) is then viewed or detected through the optics of the microscope.

Regions with more matter or stain material in the field of view will appear darker when viewed through the microscope. Thus in order to achieve a uniform colour within each discrete region, (which is key for the purposes of calibration) it is important to ensure a constant light path thickness within each discrete region.

In other words, within each region the effect is to produce a common spectral response (in terms of light frequency and intensity) to incident light, such as white light, which is independent of the position with the region at which the interaction with the incident light occurs. Typically the common optical path length for one region will be the same as that for each other region.

Ordinarily the illumination conditions of the incident light are normal to parallel upper and lower surfaces bounding the said region. The use of parallel planar surfaces is particularly beneficial in providing the common optical path length by ensuring the volume of stain material between opposing points on the respective surfaces is constant within a region. Typically each region is of the same geometry, thereby ensuring that the spectral response is caused by the stain concentration or type, or any material used to retain or localise the stain.

Fluorescent markers are typically associated with confocal, fluorescence systems. These systems focus a point source of radiation onto a small target region within a sample to eliminate out-of-focus light from regions in the sample which are beyond the focal plane. Confocal imaging permits the defined thickness of the confocal layer only to be imaged so it is possible to image the upper layer of the material without any effect from the material below the confocal layer. The entire sample is not illuminated and thus, if attempting to calibrate the system, it is not essential to ensure a constant light path thickness across the discrete region of a calibration device.

Although the calibration device according to the present invention could in principle be used in a confocal system, it is more suited to bright field systems because the optical thickness of each discrete region is controlled such that a homogenous spectral/optical response is achieved for the entire region as viewed by, typically, a transmissive imaging system. Preferably, therefore, the biological stain material used is a tissue stain, these excluding fluorescent markers.

Some discrete regions of the retaining member, or a substrate or other article to which the retaining member is attached, may contain other types of coloured material such as filter patches for example. Accordingly, it will be understood that not all discrete regions in a device need to be provided with a predetermined biological stain material, although typically this is the case in practice.

The retaining member may be adapted for use with a glass slide and also with a cover or cover slip for sealing the stain material. Typically in such cases the discrete regions are formed as recessed areas or wells, for retaining the stain material in liquid form within the wells. The one or more discrete regions wells may be machined or cast within the retaining member.

Using recesses or wells enables the localised stain materials to have substantially parallel surfaces normal to the optical axis of the imaging device to ensure a homogenous effect as viewed by the imaging system. The depth of the wells may be significantly larger than the thickness of a typical stained sample and therefore the concentration of the stain material localised in the discrete regions may be reduced accordingly.

Alternatively, the discrete regions may be provided using a masking element which has cut out regions for defining the discrete regions. The masking element may be for example a gasket which acts as a template or stencil for defining the sides of the wells. The thickness of the gasket may be chosen to define the depth of the discrete regions containing the stain material. Advantageously here, the bottom of the discrete region is flat, as it is defined by a top side of the retaining member which may be a smooth slide.

The masking member may be mounted onto the surface of the retaining member. In this case the masking element may be a glass cover slip having a number of cut out regions or holes. Advantageously, as in the above case, the bottom of the discrete region is flat, as it is defined by a top side of the retaining member which may be a smooth slide. An additional advantage is an improved accuracy for defining the size of the discrete region, as the extent of the region is defined by the holes in the cover slip. This improved definition helps to define the total volume of a region which, with accurate pipetting of the stain material into the region, helps define the thickness of the stain material more accurately. Accordingly, using this method enables a constant light path thickness across each patch.

A cover element may be provided to seal the stain material in the discrete regions upon or within the retaining member. This ensures that the stain material is localised within the discrete regions. In the case of a retaining member formed as or in association with a slide, this may include the sealing of the stain material (in liquid form) in the wells using an adhered cover slip for example. The calibration of the biological imaging system using the calibration device obtained with the invention may be performed prior to delivery of the imaging system or after installation during later maintenance procedures, over time. In the latter case the localisation of the stain material within the discrete regions is particularly important.

In some cases the retaining member may be a region of substrate upon which a stain material may be printed or fluid-jetted. Inkjet, flexographic or screen printing are well known techniques which may be used for this purpose. Alternatively, one may use spin coating or thin film deposition techniques, preferably defining the discrete regions using a masking element or by photo-etching the retaining member.

A homogeneous coverage of a discrete region may be achieved with small adjacent deposits of stain material which mix upon deposition. Surface modification techniques of the retaining member substrate may be used to encourage this. In such cases the thickness of the stain material may be less than in the corresponding samples to be scanned due to the driving off of carrier fluid following the jetting process.

The biological stain materials localised in the discrete regions may have different concentrations of a common biological stain (for example a different concentration for each region), or may include mixtures of two or more stains, for example in ranges of concentrations formed as a series. Furthermore, the biological stain materials localised in the discrete regions may have different optical thicknesses to reproduce graduation in stained tissue. This graduation may be produced for example by diluting the stain material, such that one discrete region has a different level of dilution than that of another discrete region containing the same type of stain.

Some fluid-jet materials include curable agents known in the art which may be also used to localise or stabilise the deposited material. However, in a further alternative, individual precisely deposited patches of absorbent material such as a processed form of tissue including gelatin may be used to retain the stain material. These patches are advantageous as they closely reproduce the properties of biological material. The biological material may include plant or animal material, particularly human tissue.

In a further alternative, providing the discrete regions comprises providing one or more tissue elements onto or within a carrier, dividing the carrier into one or more carrier slices wherein each carrier slice comprises the one or more tissue elements and providing the one or more slices onto the retaining member. The tissue elements may be deposited onto the carrier using known techniques to thereby form a tissue microarray (TMA). The carrier may be made from paraffin or wax for example and may be in any form, typically a block. The tissue elements are also referred to as 'cores' and may be made from donor tissue or a synthetic tissue substitute, and therefore provide the advantage of having the same or similar properties as a biological material. In this alternative the step of depositing the one or more of the predetermined tissue stations in a fluid form to the discrete region may be performed before the step of providing the discrete regions upon or within the retaining member.

A calibration device may be formed using a selection of stain materials applied to small areas of a microscope slide to make up a colour calibration chart with colour patches. The colour calibration chart can then be measured with a spectrometer, spectrophotometer or similar instrument to produce spectral data for each patch on either every slide or for a batch of slides. The spectral data may be converted into any form of calibration data including for example CIE colour coordinates such as XYZ or Lab.

A further advantage of the present invention is that the formed calibration devices may be used with available imaging systems which have an average spatial resolution of less than 50 µm. If, for example, a calibration target was produced with actual stained cells instead of the stain material used in accordance with the invention, a much higher spatial resolution would be required.

For example, if the average size of actual cells is approximately 4 µm, some areas within the cell can be less than 0.5 µm. Accordingly, using actual stained cells to create a calibration target would require the registration between the imaging system and the spectral calibration system to have a 0.5 µm spatial resolution. With the systems available in the state of the art, this would be very difficult. Advantageously, the methods in accordance with the invention provide colour charts with relatively 'flat' patches which may be imaged at lower spatial resolution. For example, if the patches are greater than 100 µm in dimension, the accuracy required for the registration between the imaging system and the spectral calibration system is greatly relaxed to less than 50 µm.

Examples of such methods will now be described in detail with reference to the following figures.

Figure 1A:
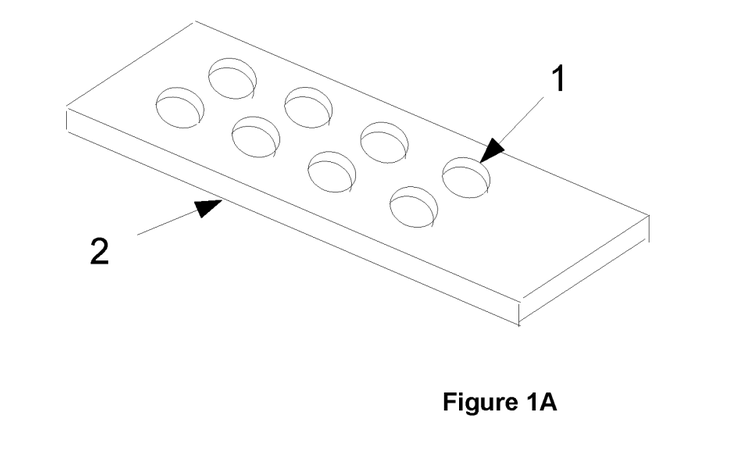
FIGS. 1A and 1B show a first exemplary method of constructing an imaging calibration device in accordance with the invention.
Figure 1B:
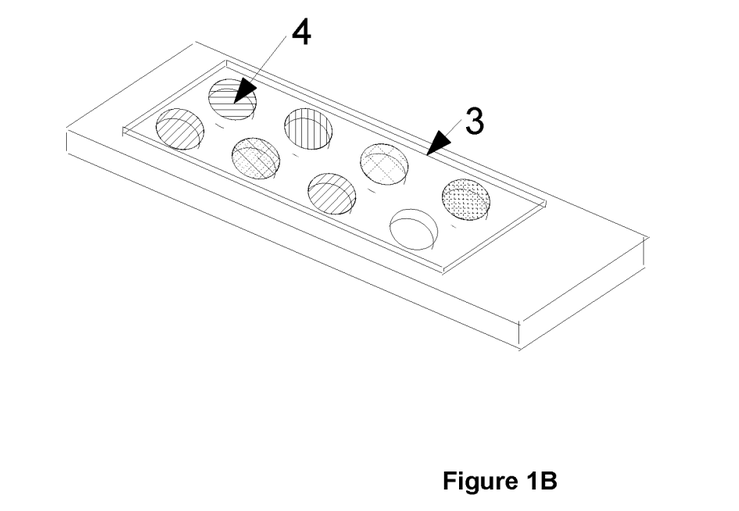

In the first exemplary method shown in FIGS. 1A and 1B, the retaining member is a slide 2, such as a microscope slide. Preferably the slide 2 is made of a suitable transparent material such as glass. Discrete regions are formed within the slide 2 as recessed areas or wells 1 located in one of the major opposing surfaces of the slide 2. Notably the slide thickness is greater than the well depths.

The wells 1 can be produced by any suitable method, such as machining into the material of the slide 2 or casting the wells into the slide 2 when the slide is manufactured. Any number of wells 1 can be provided within the slide 2. A typical slide 5 is 75 mm long and 25 mm wide, having a thickness typically around 1 to 3 mm.

In this example the wells are circular, although it would be appreciated that any shape of the well may have any shape, including square. Preferably the bottom of the wells 1 is flat so that a well has a constant depth. The depth of each well 1 (shorter than the thickness of the slide 5) is typically 0.5 to 2 mm. The width of each well (the diameter of the well in this example) is typically from 50 µm to 600 µm although well sizes covering the full width of the slide are also possible.

A predetermined tissue stain material is then deposited into each well 1 to form a colour patch (see FIG. 1B). Preferably the stain material 4 is made from a stain typically used in tissue preparation which has been "developed" to mimic interaction with the tissue. The developing varies depending on the type of cells in the tissue. For example, if a cell contains iron, it will show as blue when stained with a "Prussian blue" stain, due to interaction of the stain with iron. Hence, one needs to "pre-react" or "develop" the stain, that is treat or mix this stain, with an iron containing solution to provide the predetermined tissue stain material. However, due to their varying pH levels, other stains may simply react chemically when localised in the discrete regions and do not need to be treated with a particular solution.

Figure 2:
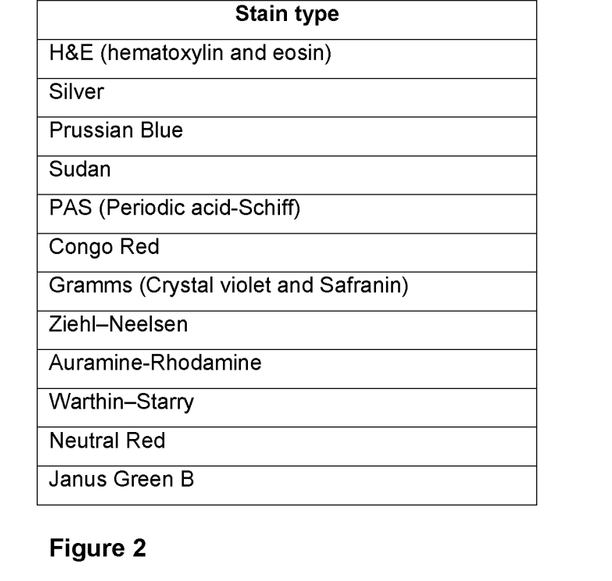
FIG. 2 is a table including a list of stains suitable for the invention.

A list of example tissue stains suitable for the methods in accordance with the invention as is listed in the table of FIG. 2. It will be appreciated that this table is not an exclusive list of suitable stains. There are a number of other stains which could be used for this process if they were stabilised by those skilled in the art so that colour did not change over the use of the chart. A typical stabilisation technique uses a pH buffer solution to control the pH level of the stain's environment.

The deposition of the predetermined biological stain material 4 into each well 1 can be performed manually with a pipette system or it can be automated with a machine. Optionally, a cover 3 may be placed over the wells 1 to act as a seal for the stain material localised in the wells 1 (see FIG. 1B). Where the cover is relatively thin, it may be referred to as a cover slip 3 or sealing layer. Preferably all of the wells 1 formed in the slide 2 are covered and thereby sealed by a single cover 3.

Figure 3:
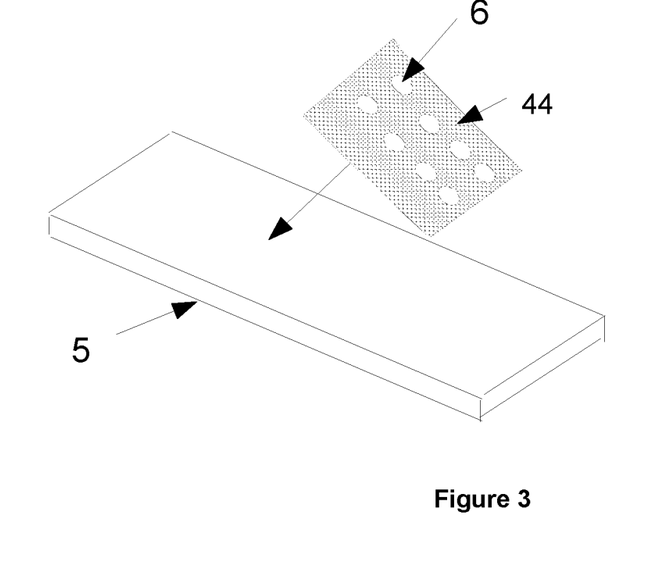
FIG. 3 shows a second exemplary method of constructing an imaging calibration device in accordance with the invention.

A second exemplary method shown in FIG. 3 uses a slide 5 as the base of the wells and the walls of the wells may be provided onto the slide 5 using a masking element, template or stencil to define the sides of the wells. In this example, the masking element is a gasket 44 with cut out regions or holes 6 for well definition. The gasket 44 is relatively thin compared to the slide 5 and therefore may be referred to as a gasket layer 44. The thickness of the gasket layer 44 may be chosen to define the depth of the wells, which is typically 0.1 to 2 mm. The gasket layer 44 may be made from any suitable material including glass, silicone, metal, or a plastic polymer for example.

The gasket layer 44 may be affixed for example by gluing to a top surface of the slide 5 and the stain material can be deposited into the formed wells using a pipette system for example. Once the wells have been filled with the stain material, the wells may be sealed with a cover slip or a sealing layer (not shown). This method has the advantage of an improved flatness of the bottom of the well as it is defined by a top side of the slide 5.

Figure 4A:
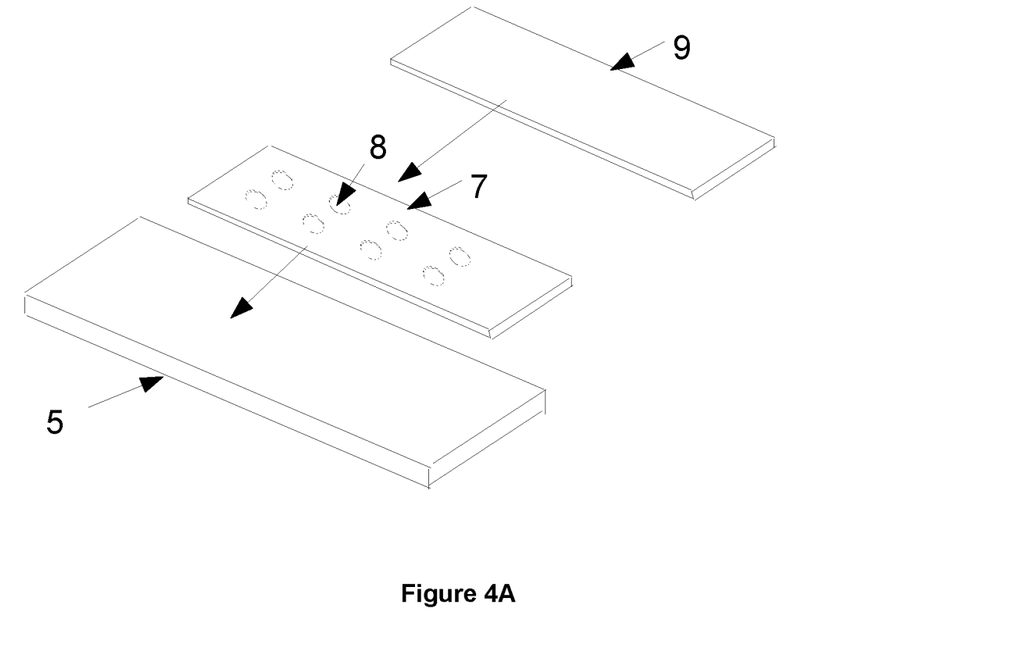
FIGS. 4A and 4B show a third exemplary method of constructing an imaging calibration device in accordance with the invention.
Figure 4B:
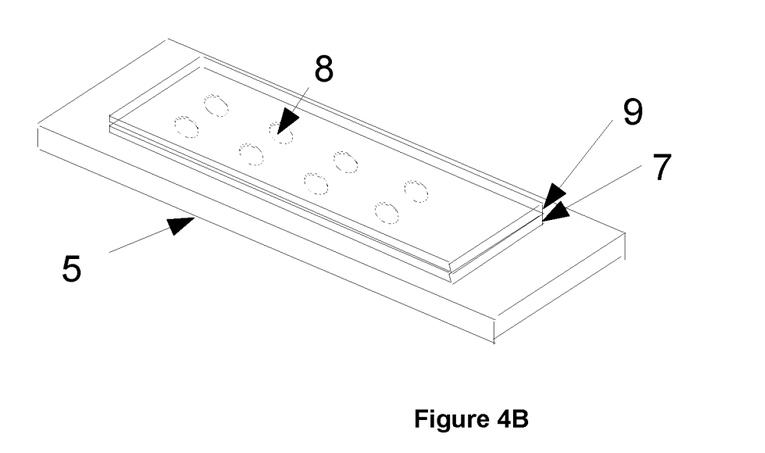

A third exemplary method shown in FIGS. 4A and 4B uses a slide 5 as the base of the wells and defines the sides of the wells by a cover or cover slip 7 which in this example is made from glass. The cover 7 has a number of cut out regions or holes 8 manufactured in the cover slip 7, thereby forming a masking element as described above in the second exemplary method.

The holes 8 may be for example machined or cast into the cover slip 7. The cover 7 is then mounted or permanently attached to the slide 5. The depth of these wells is typically 0.17 mm. The wells may be filled with the stain materials using a pipette system for example. Once the wells have been filled with the stain materials, they can be sealed with another cover slip or sealing layer 9.

This method has the advantage of an improved flatness of the bottom of the wells as it is defined by the top side of the slide 5. Additionally, by mounting the cover slip 7 onto the slide, this method provides improved accuracy for defining the well size, as the extent of the well is defined by the holes 8 in the cover slip 7. This improved definition helps to define the total volume of a well which, with accurate pipetting of the stain, helps define the thickness of the stain material provided on the slide more accurately.

Figure 5:
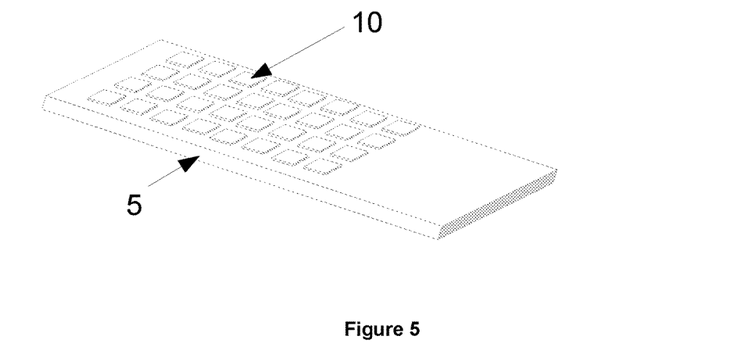
FIG. 5 shows a calibration device formed using a fourth exemplary method of constructing an imaging calibration device in accordance with the invention.

A fourth exemplary method to manufacture the imaging calibration device is to print a stain material in the form of patches 10 onto a slide 5, as shown in FIG. 5, for example with an inkjet printer. Inkjet printing is a well known technique for deposition of well controlled amounts of fluid onto a surface.

In this example, the patches 10 are square and are typically 1 mm by 1 mm in size. Depending upon the inkjet printer used, the drop volumes of inkjet printing can typically produce between 1 and 10 pL per drop which, if evenly distributed, can produce a film thickness and therefore patch thickness of 4 to 13 µm. These values are close to the thickness normally produced in stained tissue slides, which are typically 4 to 20 µm thick.

Uniform thick films printed with inkjet printers can be produced by printing multiple adjacent dots of stain material and may require some pre-treatment of the slide surface. Such techniques are well known and an example of the printing of a typical stain is published in "*Inkjet Printed Prussian Blue Films for Hydrogen Peroxide Detection*" Analytical Sciences: February 2012—Hu, Lin, Liao.

An additional alternative to manufacture the imaging calibration device is to print a stain material onto a slide with a screen printing process. A screen printing process typically produces a film thickness of 8 to 20 µm which is also similar to the thickness of stained tissue on slides. Alternatively, flexographic printing can be used, which typically produces 3 to 10 µm thick films.

As a stain only partially attaches to the tissue and the degree of adhesion is dependent upon the chemistry of the tissue, there is a continuous tonal range of the stain. For a colour chart to produce a good mapping from RGB values to defined colour space, it is desirable for this graduation to be reproduced. This graduation can be produced in the predetermined biological stain material by diluting the stain material to be printed for selected individual patches, such that at least one patch has a different level of dilution than that of another patch containing the same type of stain. The stain material may be diluted with a water based solution for example to decrease the concentration of the stain material to be printed.

The graduation can also be produced by printing a diluted solution in multiple layers (i.e. 'overprinting') onto a discrete region to form a thicker patch. To achieve the desired result, it is the optical thickness of the patch defining the amount of light absorbed by the patch which varies from patch to patch.

A further exemplary method for manufacturing the imaging calibration device may use a spin coating manufacturing process, using a slide as a substrate and a biological stain material to coat the substrate. Spin coating is a well known technique used to apply uniform thin films to flat substrates. A typical film of biological stain material produced by spin coating has a thickness of between 2 to 10 µm. The substrate is normally in the shape of a disk. One or more slides may be cut from a single disk after manufacturing the substrate.

Several techniques may be used to ensure that the stain material is localised on the substrate forming the colour patches. For example, masking or photo etching may be used to achieve deposition of the stain material in only a small area or areas of the substrate. Such techniques are well known and have been commonly used in the manufacturing of electrical circuits.

A further exemplary method for manufacturing the imaging calibration device involves coating a slide using a thin film deposition manufacturing process such as chemical vapour deposition (CVD), physical vapour deposition (PVD), chemical solution deposition (CSD) or chemical bath deposition (CBD). A typical film of biological stain material produced by this has a thickness of approximately 1 µm. Several techniques may be used to ensure that the stain material is localised on the slide forming the colour patches. For example, masking or photo etching may be used to achieve deposition of the stain material in only a small area or areas of the slide.

An alternative for manufacturing the imaging calibration device comprises depositing an absorbing material on the slide to act as a sponge or retaining agent for the stain. This method has the advantage of removing the need to pre-treat the slide prior to the provision of the stain material. Any suitable absorbing material may be used, such as collagen. Collagen is a connective tissue component and may also be used in its purified form of gelatin, which is collagen that has been hydrolysed irreversibly.

The absorbing material may be deposited on the slide using any printing technique described above to form patches of absorbing material in any desired pattern, for example a chequer board pattern. Alternatively, the absorbing material may be deposited on the slide using the spin coating technique described above and then masking or etching the slide to form the patches of absorbing material.

Once the absorbing material is deposited on the slide, each patch of absorbing material can be stained by one or more required stains in the required concentration using any of the printing or pipetting techniques described above. Each patch of absorbing material represents a discrete region on the slide and acts as a boundary for the stain material which is thus localised in the discrete region. Once all the patches of absorbing material are stained, they may be sealed with a covering layer of sealant or with a cover slip.

Figure 6:
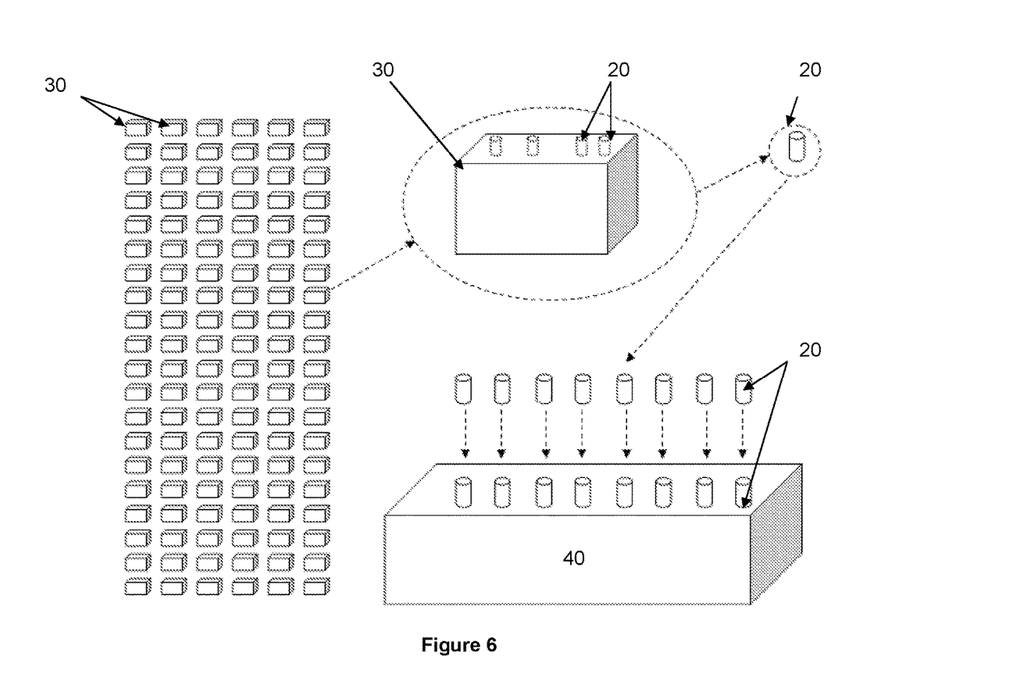
FIG. 6 shows elements of a further exemplary method of constructing an imaging calibration device in accordance with the invention.

A further method for manufacturing the imaging calibration device involves the use of tissue microarrays, TMAs, and is schematically represented in FIG. 6. As shown in FIG. 6, a number of tissue elements or cores 20 are obtained from tissue blocks 30. The tissue blocks 30 may be selected depending on the desired application and may be donor tissue or a synthetic, preferably uniform, tissue substitute such as celluloid, gelatin or similar. The cores 20 are stained with each of the stains to be used on the slide. These cores 20 are deposited into a carrier 40 which may be a block of paraffin, wax or other suitable material. The cores 20 may be deposited into the carrier 40 using commonly available methods to form a TMA. The carrier 30 may be then sliced thinly and each slice may be placed on a slide and encapsulated using one of the standard procedures commonly employed in the art.

A single slice preferably contains multiple tissue elements. To form the carrier 40, a block of paraffin for example may be cast with defined holes for the cores 20 to be inserted into. A number of cores 20 are typically inserted into the block and "fixed" by softening the block. Once the block is fixed, a slice may be produced using a suitable tool such as a microtome. Accordingly, each slice contains all of the cores 20 used to form the TMA. A slice may be then placed onto a slide 5 and then the paraffin may be evaporated by heating. A cover slip may be then placed over the slide 5 and cores 20.

When these slides are imaged by a microscope, the RGB value of each patch from the microscope image can be used with the spectral or colour data on the patch to produce a mapping from RGB to a calibration data or defined colour space such as Lab, XYZ or sRGB. The calibration data may be an ICC profile or a 3D look up table. Alternatively, a predetermined mathematical function, such as a polynomial mapping function may be used. By imaging all the patches or a subset of the patches on the calibration device, it is possible to provide a mapping from the measured RGB values to the desired colour space.

Using the manufacturing methods according to the invention as described above, the imaging calibration device or colour chart may be manufactured with a large number of patches over a large area of the slide. A typical slide would be 75 mm long by 25 mm wide with an area of 62 mm by 23 mm being suitable for imaging by an imaging device. For example, if 1 mm by 1 mm square patches were manufactured with 0.1 mm separation between the patches, over 1000 patches could be produced.

The field of view in a microscope at typical magnification used in tissue imaging may only be 1 mm by 1 mm which sees only one patch. Accordingly, more than 1000 images of the slide would need to be taken to fully image the colour chart. It would be possible to image multiple adjacent patches at once, for example four patches, but this would still require more than 250 images to image the whole colour chart. A whole slide scanner such as the SCN400 by Leica Microsystems can automate this process and the whole chart can easily be imaged for analysis. However, when using a manual microscope with no automation, it would be extremely difficult to capture over 1000 or 250 images in adequate time.

When a manual microscope is used, it is possible to image only a sub set of the patches, typically 9 to 30, to produce the mapping. By imaging four adjacent patches at once, up to 120 patches may be imaged. Although mapping with this reduced data set may not be as accurate as using all of the patches in the colour chart, it will still produce a reasonably accurate mapping.

The invention claimed is:

1. A method of forming an imaging calibration device for a bright field biological material imaging system, the method comprising:

providing one or more discrete regions of a uniform tissue substitute upon or within a retaining member, each region for the receipt of a selected non-fluorescent tissue stain material, wherein, for each discrete region, every part of the discrete region produces a common optical path length through the region, as defined in the direction normal to the surface of the retaining member;

selecting one or more non-fluorescent tissue stain materials, wherein each of the selected non-fluorescent tissue stain materials has a predetermined optical response; and depositing one or more of the selected non-fluorescent tissue stain materials in a fluid form to the said one or more discrete regions such that the said material is localised in the said region and each said discrete region produces a homogenous spectral response across the region.

2. A method of forming an imaging calibration device according to claim 1, wherein the step of providing the one or more discrete regions comprises machining or casting at least one recess area into the retaining member.

3. A method of forming an imaging calibration device according to claim 1, wherein the step of providing the one or more discrete regions comprises providing a masking element onto a surface of the retaining member, wherein the masking element has at least one cut out region for defining the one or more discrete regions.

4. A method of forming an imaging calibration device according to claim 3, wherein providing the masking element comprises mounting the masking member onto the surface of the retaining member.

5. A method of forming an imaging calibration device according to claim 1, further comprising providing a flat cover element for sealing the one or more of the selected non-fluorescent tissue stain materials upon or within the retaining member.

6. A method of forming an imaging calibration device according to claim 1, wherein providing one or more of the selected non-fluorescent tissue stain materials comprises printing the one or more of the selected non-fluorescent tissue stain materials onto a surface of the retaining member.

7. A method of forming an imaging calibration device according to claim 6, wherein printing is selected from the group consisting of inkjet printing, flexographic printing, and screen printing.

8. A method of forming an imaging calibration device according to claim 1, wherein a first non-fluorescent tissue stain material localised in a first discrete region has a first concentration of stain material which is higher than a second concentration of stain material of a second non-fluorescent tissue stain material localised in a second discrete region different from the first discrete region.

9. A method of forming an imaging calibration device according to claim 1, wherein a first non-fluorescent tissue stain material localised in a first discrete region has a first optical thickness which is higher than a second optical thickness of a second non-fluorescent tissue stain material localised in a second discrete region different from the first discrete region.

10. A method of forming an imaging calibration device according to claim 9, wherein said optical thicknesses of said non-fluorescent tissue stain materials localised in said discrete regions are arranged as a series of optical thicknesses representing a range of expected optical thicknesses from actual samples once stained.

11. A method of forming an imaging calibration device according to claim 1, wherein providing one or more of the selected non-fluorescent tissue stain materials comprises spin coating the retaining element with one or more non-fluorescent tissue stain materials.

12. A method of forming an imaging calibration device according to claim 1, wherein providing one or more of the selected non-fluorescent tissue stain materials comprises depositing a thin film onto the retaining element, wherein the thin film comprises the at least one or more non-fluorescent tissue stain materials.

13. A method of forming an imaging calibration device according to claim 11, wherein providing the one or more discrete regions comprises providing a masking element on a surface of the retaining member, wherein the masking element has at least one cut out region for defining the one or more discrete regions.

14. A method of forming an imaging calibration device according to claim 11, wherein providing the one or more discrete regions comprises photo etching the retaining member to define the one or more discrete regions.

15. A method of forming an imaging calibration device according to claim 1, wherein providing one or more discrete regions comprises providing one or more elements of stain absorbent material onto the retaining member.

16. A method of forming an imaging calibration device according to claim 1, wherein providing one or more discrete regions comprises providing one or more tissue elements onto or within a carrier, dividing the carrier into one or more carrier slices wherein each carrier slice comprises the one or more tissue elements and providing the one or more carrier slices onto the retaining member.

17. A method of calibrating an imaging calibration device formed using a method according to claim 1, the method of calibrating comprising:

measuring the at least one discrete region containing localised non-fluorescent stain material to thereby provide spectral data for each of the at least one discrete regions; and mapping one or more of said spectral data to standard colour data to thereby determine calibration data for the imaging calibration device.

18. An imaging calibration device for a bright field biological material imaging system, the device comprising:

a retaining member;

one or more discrete regions of a uniform tissue substitute located upon or within the retaining member, each region for the receipt of a selected non-fluorescent tissue stain material, wherein every part of each discrete region has a common optical path length through the region, as defined in the direction normal to the surface of the retaining member; and one or more selected non-fluorescent tissue stain materials received in the said one or more discrete regions such that the said material is localised in the said region, wherein each of the selected non-fluorescent tissue stain materials has a predetermined optical response, and wherein each discrete region produces a homogenous spectral response across the region.

19. An imaging calibration device according to claim 18, the device further comprising a masking element provided onto a surface of the retaining member, wherein the masking element has at least one cut out region for defining the one or more discrete regions.

20. An imaging calibration device according to claim 18, the device further comprising a cover element for sealing the one or more of the selected non-fluorescent tissue stain materials upon or within the retaining member.

21. An imaging calibration device according to claim 18, the device further comprising wherein a first non-fluorescent tissue stain material localised in a first discrete region has a first concentration of stain material which is higher than a second concentration of stain material of a second non-fluorescent tissue stain material localised in a second discrete region different from the first discrete region.

22. An imaging calibration device according to claim 18, wherein a first non-fluorescent tissue stain material localised in a first discrete region has a first optical thickness which is higher than a second optical thickness of a second non-fluorescent tissue stain material localised in a second discrete region different from the first discrete region.

23. An imaging calibration device according to claim 22, wherein said optical thicknesses of said non-fluorescent tissue stain materials localised in said discrete regions are arranged as a series of optical thicknesses representing a range of expected optical thicknesses from actual samples once stained.

24. A device to calibrate a bright field biological material imaging system, the device comprising:
  one or more discrete regions of a uniform tissue substitute located upon or within the retaining member, each region for the receipt of a non-fluorescent tissue stain material, wherein every part of each discrete region has a common optical path length through the region, as defined in the direction normal to the surface of the retaining member; and
  one or more non-fluorescent tissue stain materials received in the said one or more discrete regions such that the said material is localised in the said region,
  wherein each of the one or more discrete regions produces a homogenous spectral response across the region.

25. An imaging calibration device according to claim 18, wherein the uniform tissue substitute comprises celluloid or gelatin.

26. A method of forming an imaging calibration device according to claim 1, wherein the uniform tissue substitute comprises celluloid or gelatin.

27. An imaging calibration device according to claim 18, wherein the uniform tissue substitute comprises cellulose or gelatin.

* * * * *